United States Patent [19]

Davidow et al.

[11] Patent Number: 4,880,741

[45] Date of Patent: Nov. 14, 1989

[54] PROCESS FOR TRANSFORMATION OF YARROWIA LIPOLYTICA

[75] Inventors: Lance S. Davidow, Groton; John R. DeZeeuw, Stonington, both of Conn.

[73] Assignee: Pfizer Inc., New York, N.Y.

[21] Appl. No.: 634,505

[22] Filed: Jul. 25, 1984

Related U.S. Application Data

[63] Continuation-in-part of Ser. No. 539,591, Oct. 6, 1983, abandoned.

[51] Int. Cl.$^4$ .................. C12N 15/00; C12N 1/16; C12N 1/20; C12P 19/34
[52] U.S. Cl. .................. 435/172.3; 435/320; 435/255; 435/252.33; 435/91; 935/28; 935/29; 935/69; 935/73; 935/56
[58] Field of Search .................. 435/172.3, 320, 253, 435/255, 91; 935/27, 28, 29, 69, 73, 56

[56] References Cited

U.S. PATENT DOCUMENTS

| | | | |
|---|---|---|---|
| 4,394,443 | 7/1983 | Weissman et al. | 435/68 |
| 4,407,953 | 10/1983 | DeZeeuw et al. | 435/145 |
| 4,628,033 | 12/1986 | DeZeeuw et al. | 435/255 |

OTHER PUBLICATIONS

Davidow, L. et al., *Curr. Genetics*, vol. 10, pp. 39–48, 1985.
Ogrydziak, D. et al., *J. Cell. Biochem.*, Supp. 9C, Abstracts, UCLA Symposia on Molecular & Cellular Biology, Apr. 6–25, Abstract #1622, p. 193, 1985.
Ogrydziak, D. et al., *J. Gen. Microbiol.*, vol. 28, pp. 1225–1234, 1982.
Hinnen, A. et al., *Proc. Natl. Acad. Sci.*, vol. 75, No. 4, pp. 1929–1933, 1978.
Beggs, J., *Nature*, vol. 275, pp. 104–109, 1978.
Ogrydziak, D. et al., *Mol. Gen. Genet.*, vol. 188, pp. 179–183, 1982.
Van der Walt et al., *Antonie Van Leeuwenhock*, vol. 46, pp. 517–521, 1980.
Botstein, D. et al., in *The Molecular Biology of the Yeast Saccharomyces*, pp. 607 and 615–623, 1982, (Cold Spring Harbor Laboratory).
Mantiatis, T. et al., in *Molecular Cloning*, (Cold Spring Harbor Laboratory), pp. 3–5 and 13–15, 1982.
Hinnen et al., in "Overproduction of Microbiol Products", (Eds. Krumphanzl et al.), pp. 381–393 (1982), Academic Press, New York.
Ratzkin et al., *Proc. Natl. Acad. Sci.*, 74, 487–491 (1977).
S. Das et al., *Curr. Gent.*, 6, 123–128 (1982).
Beach et al., *Nature*, 290, No. 5802, 140–142 (1981).
Orr-Weaver et al., *Proc. Natl. Acad. Sci.*, 78, 6354–6358 (1981).
Hinnen et al., in "Gene Cloning in Organisms Other than *E. coli*", Edited by Hofschneider and Goebel, pp. 101–106, Springer-Verlag (1982).

*Primary Examiner*—Jayme A. Huleatt
*Attorney, Agent, or Firm*—Peter C. Richardson; J. Trevor Lumb; Gregg C. Benson

[57] ABSTRACT

Process for transformation of *Yarrowia lipolytica*, vectors useful therefor comprising DNA of a microbial vector and chromosomal DNA of *Y. lipolytica* and transformants comprising said vectors in *E. coli* and *Y. lipolytica*, and integrative shuttle vectors for *Escherichia-Yarrowia* transgeneric cloning. Said vectors or subclones thereof enable creation of *Y. lipolytica* cloning vectors into which specific or random segments of DNA can be inserted and the resulting vectors used to transform a suitable host microbe, especially *Y. lipolytica*, to improve the fermentation characteristics thereof and hence their industrial utilization.

The methodology described permits the cloning of genes from a gene library of *Y. lipolytica* by complementation with an integrating vector.

87 Claims, 7 Drawing Sheets

PROCESS FOR TRANSFORMATION OF YARROWIA LIPOLYTICA

CROSS-REFERENCE TO RELATED APPLICATION

This application is a continuation-in-part of co-pending application Ser. No. 539,591, filed Oct. 6, 1983, now abandoned.

BACKGROUND OF THE INVENTION

1. Field of the Invention

This invention relates to a process for the transformation of *Yarrowia lipolytica* to improve its utilization for industrial purposes; to vectors and subclones thereof useful therefor, especially to vectors which replicate autonomously in *Escherichia coli* and integrate but do not replicate autonomously in *Yarrowia lipolytica*; to transformants of *E. coli* and *Y. lipolytica* containing said vectors and to their use for producing proteins.

2. Description of the Prior Art

Major emphasis in molecular cloning has been directed to prokaryotes, particularly *E. coli*, and more recently *Bacillus subtilis*, as host organisms. *E. coli*, despite its extensive use as host organism for the cloning and expression of heterologous DNA, is known to pose certain problems, such as failure to secrete proteins into its growth medium with subsequent ease of isolation thereof. The proteins thus produced intracellularly are usually not in their native state and are found as insoluble aggregates called inclusion bodies. The possible need to destroy the cells to recover the protein raises the possibility of contamination thereof with a toxic substance.

In view of the cited difficulties, *B. subtilis* has been turned to as an alternative host organism since it secretes protein and does not produce toxins. However, as host organism, *B. subtilis* is subject to certain limitations; instability of transformed strains resulting in loss of heterologous DNA, and the frequent reduction in the ability of the entering DNA to coexist with the host DNA.

In recognition of the above-mentioned difficulties with prokaryotes as host organisms, attention shifted to eukaryotes, and specifically yeasts, as host organisms. Yeasts of industrial importance, are non-toxic and can be grown to very high densities. Some species are well analyzed genetically and some species can secrete proteins.

The first transformation of a yeast, *Saccharomyces cerevisiae*, was reported by Hinnen et al., Proc. Natl. Acad. Sci., 75, 1929–1933 (1978) who demonstrated that a cloned segment of yeast DNA encoding the LEU2 locus could transform a nonreverting leu2− mutant of yeast to a LEU+ phenotype. This transformation was shown to result from integration into the chromosome of the plasmid containing the LEU2 segment of DNA. The integration involved recombination between homologous segments of DNA.

Hinnen et al. in "Overproduction of Microbial Products", edited by Krumphanzl et al., Academic Press, N.Y., Ch. 30, 1982, present a review of yeast transformation procedures. A prerequisite to yeast transformation was described by Ratzkin et al., Proc. Natl. Acad. Sci. 74, 487–491 (1977) in their cloning of yeast (*Saccharomyces cerevisiae*) LEU2 by complementation of an *E. coli* leuB mutation.

Sjostak et al., Plasmid 2, 536–554 (1979) describe the construction of plasmids containing the LEU2 gene of yeast and fragments of rDNA and the integration of the plasmids into the rDNA locus following yeast transformation. The basic thrust of their investigation involved the integration of a genetic marker, the LEU2 gene, inserted into the rDNA locus, as a genetic marker for mapping the rDNA. One of the reported plasmids, pSZ20, containing the BglII-B fragment of rDNA and the SalI-XhoI LEU2 fragment, is identified as a useful vector for cloning fragments of yeast DNA in yeast.

Orr-Weaver et al., Proc. Natl. Acad. Sci., 78, 6354–6358 (1981) demonstrated high frequency integration of linear plasmids derived from pBR322, all of which are nonreplicating in yeast and transform only by integration, in *Saccharomyces cerevisiae* when the plasmids are cut within DNA sequences homologous to the yeast chromosome.

*Yarrowia lipolytica*, an industrially important species of yeast, is used to produce citric acid and single cell protein. It can also be used to produce erythritol, mannitol and isopropylmalic acid. *Y. lipolytica* suffers from certain inherent deficiences, such as its limited spectrum of utilizable carbon sources. The overall value of *Y. lipolytica* could be increased by eliminating such deficiency as, for example, by introducing correcting DNA from another species. *Y. lipolytica* is of special interest and value because of its ability to secrete proteins (alkaline protease, acid protease and RNAse) into its growth medium, thus permitting potential recovery of heterologous proteins in the native state without the need of disrupting the producing cells.

A highly efficient system for transformation of *S. cerevisiae* comprising a replicating hybrid plasmid, a *S. cerevisiae*—*E. coli* hybrid plasmid, which may be selected in and recovered from both *E. coli* and *S. cerevisiae* is described by Beggs, Nature 275, 104–109 (1978). High frequency transformation systems for *Schizosaccharomyces pombe* and *Kluyveromyces lactis* are reported by Beach et al., Nature 290, 140–142 (1981) and by Das et al., Current Genetics 6, 123–128 (1982), respectively.

SUMMARY OF THE INVENTION

There has now been found a process for the transformation of *Y. lipolytica* by introducing therein DNA comprising a region of homology to said *Y. lipolytica* and a detectable genetic marker. Of particular interest is the process which comprises introducing into said *Y. lipolytica* a fragment of *Y. lipolytica* DNA or, alternatively and preferably, a vector containing or including a fragment of *Y. lipolytica* DNA, said DNA or vector being detectable in said *Y. lipolytica*, vectors useful therefor, and microbial transformants comprising said vectors. In general in this transformation process, said *Y. lipolytica* DNA fragment contains a selectable marker which functions in *Y. lipolytica*, especially in *Y. lipolytica* having a mutation in the gene corresponding to said selectable marker. Of particular interest and value to this invention is the use of a *Y. lipolytica* DNA fragment having a gene coding for a biosynthetic or metabolic enzyme, such as the LEU2 gene (codes for the enzyme beta-isopropylmalate dehydrogenase, EC1.1.1.85) or the HIS1 gene (codes for the enzyme ATP phosphoribosyltransferase, EC2.4.2.17), or the URA3 gene (codes for the enzyme orotidine-5′-phosphate decarboxylase, EC4.1.1.23), or the XPR2 gene (codes for the enzyme alkaline extracellular protease, EC3.4.21.14)

and *Y. lipolytica* strains having a leu2−, a his1−, a ura3− or a xpr2− mutation, respectively.

The novel plasmids (or vectors, the terms are used interchangeably herein) described in this application have several characteristics in common; a bacterial replicon which permits their amplification in *E. coli*; the presence of a selectable genetic marker detectable in and functional in *E. coli* the presence of a structural gene which functions physiologically in *Y. lipolytica* and frequently in *E. coli*, and the presence of *Y. lipolytica* DNA fragments which provide for their integration into the genome of *Y. lipolytica*.

In general, for purposes of this invention, the production of useful vectors is based upon preparation of hybrid vectors; i.e., vectors which function physiologically in a heterologous microorganism (i.e., any species other than *Y. lipolytica*), desirably a bacterium, and preferably *E. coli*, and also in *Y. lipolytica*. Such vectors comprise microbial DNA and fragments of chromosomal DNA of *Y. lipolvtica* which fragments contain at least one selectable genetic marker; that is, a gene which functions in and is detectable in *Y. lipolytica*. The thus constructed vectors interact with homologous chromosomal sequences in *Y. lipolytica* becoming integrated into a chromosome thereof, thus achieving transformation.

As those skilled in the art will recognize, the formation of vectors containing more than one gene of yeast origin increases the likelihood of forming, from said vectors, integrants; i.e., transformants comprising said vectors, and especially of integrants having more than one gene. The presence of multiple genes, of course, increases and improves the ability to detect the presence of the vector in a yeast.

Integration is achieved with circular, linear and gapped-linear forms of said vectors. Linear and gapped-linear vectors integrate with higher efficiency than do circular vectors. The vectors desirably, therefore, have a unique restriction site; i.e., a site not present in the original microbial DNA vector or elsewhere in the *Y. lipolytica* fragment component of the vector. Linearization of the vector at such a site generates double stranded DNA having highly recombinogenic ends capable of transforming *Y. lipolytica* by integration at homologous chromosomal sequences. As Orr-Weaver et al. (loc. cit.) have shown in *S. cerevisiae*, gapped-linear plasmids are also capable of integration. Such plasmids are prepared by making two restriction enzyme cuts within the *Y. lipolytica* chromosomal DNA segment of the vector. In the case of pLD25 described below, the presence of two BglII sites conveniently allows preparation of gapped-linear plasmids.

The value of the vectors of this invention is based upon the presence therein of a selectable genetic marker, detectable in and functional in *Y. lipolytica*, hence, a detectable marker. Suitable markers are the following *Y. lipolytica* genes: LEU2, ADE1, URA3, XPR2 and HIS1, but as those skilled in the art will recognize any *Y. lipolytica* gene which affords a selection can be used. The LEU2 gene, all or a part thereof, is especially valuable. Said gene or part thereof is obtained from *Y. lipolytica* by a partial digest of the chromosomal DNA of *Y. lipolytica* by a suitable restriction endonuclease, for example, Sau3A. Said vectors or subclones thereof permit creation of *Y. lipolytica* cloning vectors by inserting therein random segments of DNA by known methodology. The resulting vectors are then used to transform *Y. lipolytica* strains having a mutation in the gene corresponding to the selectable marker. The transforming DNA having such a *Y. lipolytica* marker can provide selective growth advantage to the recipient or correct for an auxotrophic mutation in the recipient.

It is generally preferred to employ a *Y. lipolytica* DNA fragment which contains the entire LEU2 gene since said fragment permits preparation of a vector which functions physiologically in both *E. coli* and *Y. lipolytica*. However, use of a *Y. lipolytica* DNA fragment having the entire LEU2 gene is not necessary for successful conduct of the process of this invention. It is only necessary to employ a DNA fragment that includes a sufficient amount of the wild-type sequence to yield a wild-type gene upon integration in the recipient. Said fragment, while not functional in *E. coli* is detectable in *Y. lipolytica*.

Also valuable for the preparation of vectors useful in this invention are fragments of *Y. lipolytica* DNA obtained by a complete BamH1 digest of *Y. lipolytica* chromosomal DNA and which include the HIS1 gene or by a partial Sau3A digest of *Y. lipolytica* chromosomal DNA and which include the URA3 gene thereof. Said fragments contain ligatable termini, and when ligated with linearized, e.g. using BamH1, YEp24, an *E. coli—S. cerevisiae* vector, (Botstein et al., Gene 8, 17–24, 1979) afford hybrid vectors carrying the HIS1 gene or URA3 gene.

Using the novel vectors described herein, random segments of *Y. lipolytica* can be inserted therein by the "shotgun" technique. The resulting vectors can be used to transform various mutants and transformants selected by standard methods. For example, LEU2 containing vectors can be used to clone other *Y. lipolytica* genes, such as URA3. The resulting cloned URA3 gene in any transformants selected can then be subcloned away from the LEU2 gene and used as an effective *Y. lipolytica* vector.

In general a bacterial, e.g. *E. coli*, plasmid replication origin and a selective genetic marker for said bacterium are combined by known methodology with all or part of a *Y. lipolytica* gene which can be selected for, and detected, in *Y. lipolytica*. The *E. coli* cloning system is especially useful since it readily affords large amounts (bulk) of plasmid DNA by growth and amplification in *E. coli*; and permits construction of vectors and gene libraries in *E. coli*.

The herein described plasmids are useful as vectors in recombinant DNA methodology. Various genes can be inserted into them by, for example, cleaving them with a suitable restriction endonuclease to provide linear DNA having ligatable termini followed by reacting said linear DNA with an exogenous gene having ligatable termini. The resulting plasmids are then transformed into a suitable host microorganism, e.g. yeasts such as *S. cerevisiae* and *Y. lipolytica* which, upon culturing under appropriate conditions, produces the desired product. Plasmids pLD25 and pLD28 each of which contains the LEU2 gene from *Y. lipolytica*, can be selected in and detected in a *Y. lipolytica* recipient. They can thus be used to enable the creation of *Y. lipolytica* cloning vectors.

Additionally, the herein described plasmids afford means for improving fermentation characteristics of microorganisms, especially of *Y. lipolytica*, to improve the industrial usefulness by overcoming inherent deficiencies therein. For example, genes coding for utilization of various carbon sources can be introduced into them and the resulting plasmid transformed into a suitable host such as *Y. lipolytica* to modify the nutritional characteristics of said host, thus broadening the spectrum of utilizable carbon sources of *Y. lipolytica*.

The vectors, e.g. plasmids or cosmids, needed for this purpose can be constructed by techniques familiar to those skilled in the art of recombinant DNA technology. The *Y. lipolytica* DNA sequence coding for a particular periplasmic enzyme is isolated by known methods and inserted into, for example, pLD25 or a derivative thereof. A desired structural gene, for example, the maltase gene, can appropriately be fused into the DNA sequence for a periplasmic enzyme and the resulting plasmid transformed into *Y. lipolytica* and integrated into one of *Y. lipolytica*'s chromosomes by the process of this invention. The thus-produced transformant upon culturing will be capable of hydrolyzing maltose into glucose, a desirable property not possessed by the parent.

Plasmid pLD25 replicates autonomously in *E. coli* and integrates but does not replicate autonomously in *Y. lipolytica*. It is obtained by inserting into *E. coli* replicating plasmid pBR322 a *Y. lipolytica* DNA fragment desirably endowed with two distinctive properties; first, the presence of a structural gene which functions physiologically in *Y. lipolytica* and preferably also in *E. coli* and which is detectable in *Y. lipolytica*; second, possession of a unique restriction site (i.e., not present in the original *E. coli* plasmid or elsewhere in the *Y. lipolytica* host fragment) in a region flanking the DNA sequence which is introduced into the *Y. lipolytica* host strain for the purpose of correcting defects in the structural gene of said host. In order to achieve high frequency of transformation possession of a unique restriction site is essential.

Plasmids pLD21 and pLD23 described below, each of which carries the HIS1 gene of *Y. lipolytica* are obtained by inserting into YEp24 and pBR322, respectively, a fragment obtained by the complete BamHI digestion of chromosomal DNA of *Y. lipolytica*.

Plasmid pLD25 contains a fragment of *Y. lipolytica* DNA that complements *E. coli* leuB⁻ mutations, and plasmids pLD21 and pLD23 a fragment that complements *E. coli* hisG⁻ mutations.

Plasmid pLD28 also replicates autonomously in *E. coli* and integrates but does not replicate autonomously in *Y. lipolytica*. It is constructed by insertion of a SalI fragment that contains the *Y. lipolytica* LEU2 gene into the SalI site of YEp24. It is an integrating vector in *Y. lipolytica*, as noted, selectable in a leu2 mutant, a multicopy plasmid in *S. cerevisiae* selectable in a ura3 or a leu2 mutant, and a multicopy plasmid in *E. coli* selectable by ampicillin-resistance or by adequate function of the *S. cerevisiae* URA3 gene in a pyrF mutant or least effidiently by the poor although detectable function of the *Y. lipolytica* LEU2 gene in a leuB mutant.

Plasmids pLD25 and pLD28 are shuttle vectors for *E. coli* and *Y. lipolytica*. They contain both bacterial sequences that enable DNA replication in *E. coli* and sequences that enable integration in yeast; i.e., they contain an *E. coli* origin of replication and a *Y. lipolytica* region of homology. The term "shuttle" is used to indicate that said vectors constructed in *E. coli* can be integrated into *Y. lipolytica* chromosomes and reintroduced back into *E. coli* to complete the cycle. Plasmid pLD28 is also a shuttle vector for *S. cerevisiae*. These shuttle vectors make possible the cloning of *Y. lipolytica* genes by complementation of mutations in *E. coli* and by direct complementation of mutants in *S. cerevisiae* or *Y. lipolytica*. These phenomena indicate that a functional LEU2 gene product is being formed in both heterologous systems. This finding of direct complementation in *Y. lipolytica* now permits the cloning of any gene for which a mutation can be identified.

Plasmid pLD40, described below, was constructed by inserting into the EcoR1 site of pBR322 a small segment containing the LEU2 region of *Y. lipolytica*, said segment being obtained by a partial EcoR1 digest of pLD25. Plasmid pLD55, a URA3 containing plasmid, was obtained by inserting into the BamHI site of pLD40 the URA3 gene of *Y. lipblytica*.

REFERENCE TO THE DRAWINGS

FIG. 1. Sau3A partial digest gene library of *Y. lipolytica* in pBR32. This agarose gel shows that the library (marked LIB) contains some pBR322 supercoiled plasmid without insert DNA migrating just above the 2.3 kb lambda-HindIII standard (marked STD), while the remainder of the molecules contain diverse (4–10 kb) size-fractionated inserts of *Y. lipolytica* DNA migrating as a nearly continuous smear above the 4.3 kb standard. The lane in between contains an uncut plasmid (pLD21) and shows two discrete bands.

FIG. 2. Southern hybridization of EcoRI digested *Y. lipolytica* bulk DNA and pLD25 probed with radioactive pLD25. The three internal bands labelled b, c, and d of pLD25 show homology to identically sized pieces of total *Y. lipolytica* DNA. Two additional, fainter bands (labelled 1 and 2) in the *Y. lipolytica* lane probably have homology to the small *Y. lipolytica* portions of plasmid bands a and e. The lane marked "STD" contains lambda-HindIII size standards. The lane marked "P" contains approximately 2 ng of EcoRI digesed pLD25. The lane marked "Y1" contains approximately 1 microgram of total *Y. lipolytica* DNA. In a similar Southern experiment using pBR322 as a probe, only bands a and e from pLD25 hybridized.

FIG. 3. Restriction Map of pLD25. A partial restriction map based on single and some double restriction digests is shown. Sites enclosed in brackets have not been ordered with respect to each other. All sizes indicated are approximations based on agarose gel observations. The thin line represents pBR322 DNA (in the standard format with the EcoRI site at 12 o'clock) and the thick line represents insert DNA from *Y. lipolytica*. The insert has 3 EcoRV (RV), 8 AvaI (A—but only one has been mapped), 1 SphI (Sp), 1 KpnI (K), 2 SalI (S), 4 EcoRI (RI), 2 XhoI (X) and 2 close-together BglII (B) sites. The insert lacks HindIII, ClaI, BamHI and NruI sites. A 2.3 kb subclone with EcoRI ends, marked leu2 is functional in *E. coli* in only 1 orientation in the EcoRI site of pBR322.

FIG. 4. Southern hybridization of HindIII digested bulk DNA from *Y. lipolytica* transformants with radioactive pBR322 probe. HindIII digests of total DNA isolated from four different transformants and the parent strain were run on an agarose gel, blotted and probed with labelled pBR322. *Y. lipolytica* transformant #6 was randomly chosen from a culture transformed with intact, circular pLD25. Transformants 11, 12 and 15 were from a culture transformed with KpnI-linearized pLD25. All *Y. lipolytica* transformants gave two bands of hybridization, a stronger one (1) of greater than 23 kb length and a fainter one (2) the same size as the 9.3 kb lambda-HindIII standard. The lane marked PC contained parental (PC30827; ATCC 20688) DNA with no significant hybridization to the probe.

FIG. 5. Restriction Digests of pLD23 and pLD24. This agarose gel contains lambda-HindIII size standards in the outer left lane, and (a) EcoRI, (b) BamHI, (c) no enzyme treatments of pLD23 (complements *E. coli* hisG mutants) and pLD24 (fails to complement) respectively. Each lane b contains two close-together BamHI bands: the larger corresponding to pBR322 and the slightly smaller band (approximately 4 kb) representing the *Y. lipolytica* BamHI insert. The EcoRI digests show that the *Y. lipolytica* piece is in opposite orientations in the two plasmids.

FIG. 6. Restriction Map of pLD28. In addition to a 5.3 kb *Y. lipolytica* SalI piece containing the LEU2 region, this plasmid contains a 2.2 kb EcoRI piece with the origin of replication from the yeast two-micron plasmid and a 1.1 kb HindIII piece with the *S. cerevisiae* URA3 gene inserted into the corresponding sites of pBR322.

FIG. 7. Restriction Map of pLD40. The restriction site abbreviations are as in the previous figures. In addition, sites for NcoI (N), ApaI (Ap), and BstXI (Bs) have been mapped. The *Y. lipolytica* LEU2-containing segment is between 2.3 and 2.4 kb long and was inserted into the EcoRI site of pBR322. The restriction sites in pBR322 are not shown.

FIG. 8. Restriction Digests of pLD55 Compared with pLD40. The lanes of this gel (in addition to the lambda-HindIII size-standards) are (a) undigested pLD40 (b) ApaI-digested pLD40 (c) EcoRI-digested pLD40 (d) EcoRI-digested pLD55 (e) ApaI-digested pLD55 and (f) undigested pLD55. These digests indicate that the cloned URA3-containing region has two EcoRI sites and is approximately 4 kb long.

DETAILED DESCRIPTION OF THE INVENTION

The Plasmids

Figure 1:
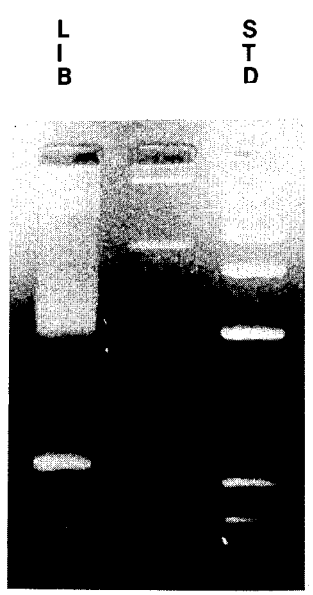

Plasmid pLD25 contains selectable genetic markers for *E. coli* and *Y. lipolytica* and is derived from the *E. coli* replicating plasmid pBR322, a multicopy plasmid. It was constructed by inserting into the BamHI site of pBR322, ca. 6.6 kb fragment obtained by a partial digestion of *Y. lipolytica* chromosomal DNA by Sau3A. Plasmid pLD28, a subclone of pLD25, also contains selectable genetic markers for *E. coli* and *Y. lipolytica*, and also for *S. cerevisiae* and is derived from YEp24. It was constructed by insertion of the approximately 5.3 kb SalI fragment that contains the *Y. lipolytica* LEU2 gene into the SalI site of YEp24.

Plasmid pLD40, also a subclone of pLD25, was constructed by insertion of the 2.3 or 2.4 kb EcoRI partial digest fragment from pLD25 into the EcoRI site of pBR322.

The Microorganisms

Microorganisms used were a strain of *E. coli* and a strain of *Y. lipolytica*, which strains are identified in the culture collection of Pfizer Inc. as *E. coli* JC-355 [Clark et al., Molec. Gen. Genet. 105, 1 (1969) obtained as strain No. 869 from the *E. coli* Genetic Stock Center, Yale University], and *Y. lipolytica* PC-30827, respectively. Said *Y. lipolytica* is the subject of application Ser. No. 539,363 cf J. R. DeZeeuw, filed Oct. 6, 1983, now U.S. Pat. No. 4,628,033, issued Dec. 9, 1986. A further microorganism, *E. coli* MC1061, utilized in the production of a gene library of *Y. lipolytica* in vector pBR322 is described by Casadaban et al., J. Mol. Biol. 138, 179–207 (1980). It is particularly useful for this purpose because of its ability to achieve high frequency of transformation. Other microorganisms can be used in place of said *E. coli* MC1061. Representative of suitable microorganisms are strains of *E. coli* which are restriction minus, such as *E. coli* HB101 (NRRLB-11371), also available as ATCC 33694, and which can be made competent for transformation.

A strain of *E. coli* defective in leucine and uracil genes (DB 6507, ATCC 35673 a Tn5 insertion mutant of HB101, from D. Botstein) is leuB pyrF74::Tn5 hsdR⁻M⁻ and also requires proline.

The following microorganisms have been deposited in, and are available from, the permanent collection of the American Type Culture Collection, Rockville, Md., U.S.A.:

| ATCC 20688 | *Yarrowia lipolytica* PC-30827 |
| ATCC 20687 | *Yarrowia lipolytica* PC-30827 transformant with pLD25 |
| ATCC 39464 | *Escherichia coli* JC-355 transformant with pLD25. |
| ATCC 20718 | *Yarrowia lipolytica* PC-30827 transformant with pLD55. |

They have been deposited under the terms of the Budapest Treaty in the American Type Culture Collection, Rockville, Md., a recognized depository affording permanence of the deposits and ready accessibility thereto by the public if a patent is granted on this application. The deposits are available during pendency of this application to one determined by the Commissioner of the United States Patent and Trademark Office to be entitled thereto under 37 CFR 1.14 and 35 USC 122, and in accordance with foreign patent laws in countries wherein counterparts of this application, or its progeny, are filed. All restrictions on the availability to the public of the microorganisms deposited will be irrevocably removed upon granting of the patent.

The taxonomic study of *Y. lipolytica* ATCC 20688 was conducted by Dr. L. H. Huang who provided the description given below. The media and methods used are those recommended by J. Lodder in "The Yeasts", second edition, N. Holland Publishing Co., Amsterdam, 1970.

CBS 599, the type culture for the species Candida lipolytica, [also known as *Saccharomycopsis lipolytica*; now classified as *Yarrowia lipolytica* (Wickerham et al.) by van der Walt and von Arx, Antonie van Leeuwenhoek 46, 517–521, 1980], was run for comparison.

Since strain PC-30827 requires leucine and uracil (J. R. DeZeeuw), both leucine ethyl ester and uracil at concentrations of 149 mg/L and 20 mg/L, respectively, were added to the following defined media: basal medium for assimilation of carbon compounds, the broth for assimilation of potassium nitrate, the vitamin-free broth for growth and the broth for testing the effect of vitamins on growth stimulation. Leucine ethyl ester as compared to leucine is slowly utilized as a carbon source. The other media were organic in nature and should support growth without the supplements. In strain CBS-599 the above-mentioned defined media with and without the supplements were also used.

As shown in the descriptions which follow, the cultures shared most of the cultural and morphological characteristics in common. A few differences were noticed. For example, the streak culture of strain CBS-599 on glucose-yeast extract-peptone agar was slightly roughened or slightly wrinkled, that of strain PC-30827 finely wrinkled. Strain PC-30827 showed poor growth on corn meal agar and produced less true mycelium when compared with strain CBS-599.

In strain CBS-599, the results in which the defined media were supplemented with leucine ethyl ester and uracil were the same as those without the supplements except that citric acid was utilized without the supplements but not in the medium with the supplements. This indicates that the supplements were not used as either carbon or nitrogen sources; thus their addition to the defined media for strain PC-30827 is acceptable.

Compared with strain CBS-599, strain PC-30827 showed no to weak rather than good growth on succinic acid, D-glucitol, and glycerol; no rather than weak growth on vitamin-free medium and salicin; no to weak rather than good growth on thiamine for growth stimulation. Strain PC-30827 failed to grow on L-sorbose whereas the reverse was true for strain CBS-599.

The several differences in biochemical tests between strain PC-30827 and CBS-599 were quantitative in nature. The mutant strain PC-30827 shared most of the biochemical tests in common with the type culture CBS-599. When the results were used in a key to the species of Candida proposed by van Uden and Buckley in *The Yeasts*, Ed. J. Lodder, 1970, each of the two strains was keyed to *Candida lipolytica* - the imperfect state of *Yarrowia lipolytica*.

Strain CBS-599

Growth on glucose-yeast extract-peptone water: After 3 days at 28° C. the cells are ovoid, elongated ovoid to elongated, with one to three buds. The ovoid cells measure 5–16×3–7 μm; the elongated cells measure up to 30 μm long. Pseudomycelium present; a pellicle present; sediment.

Growth on glucose-yeast extract-peptone agar: After one month at 28° C. the culture is cream, raised, slightly roughened or slightly wrinkled, with a dull or moist surface.

Dalmau plate cultures on corn meal agar: Growth moderate, off-white. Pseudomycelium and true, septate mycelium are present. Single, paired or three ovoid blastospores are formed terminally or pleurally on the hyphae or pseudohyphae, sometimes in a verticillate fashion.

Fermentation: Negative on glucose, galactose, sucrose, maltose, trehalose and lactose.

| Assimilation of carbon compounds: Basal medium (basal medium plus leucine ethyl ester and uracil) | | | | | |
|---|---|---|---|---|---|
| Glucose | +(+) | Soluble starch | −(−) | Ribitol | −(−) |
| Galactose | −(−) | | | Galactitol | −(−) |
| L-Sorbose | +(+) | D-Xylose | −(−) | D-Mannitol | +(+) |
| Sucrose | −(−) | L-Arabinose | −(−) | D-Glucitol | +(+) |
| Maltose | −(−) | D-Arabinose | −(−) | Salicin | − to weak |
| Cellobiose | −(−) | D-Ribose | weak(weak) | | (− to weak) |
| Trehalose | −(−) | L-Rhamnose | −(−) | DL-Lactic acid | weak (+) |
| Lactose | −(−) | Ethanol | +(+) | | |
| Mellibiose | −(−) | Glycerol | +(+) | alpha-methyl-D-Glucoside | −(−) |
| Raffinose | −(−) | Erythritol | +(+) | | |
| Melezitose | −(−) | Inositol | −(−) | Succinic acid | +(+) |
| Citric acid | +(−) | | | | |

Assimilation of potassum nitrate (with or without leucine ethyl ester and uracil): Negative.

Growth in vitamin-free medium (with or without leucine ethyl ester and uracil): Weak growth.

Vitamin stimulating growth: Thiamine in broths with or without leucine ethyl ester and uracil stimulates growth.

Sodium chloride tolerance: 11%–12%.

Maximum temperature of growth: Between 37° C. and 45° C.

Strain PC-30827

Growth in glucose-Yeast extract-peptone water: After 3 days at 28° C. the cells are ovoid, elongated ovoid, elongated, rarely elliptical, with one to three buds. The ovoid cells measure 5–14×3–6 μm; the elongated cells measure up to 25 μm long. Pseudomycelium present; a pellicle present; sediment.

Growth on glucose-yeast extract-peptone agar: After one month at 28° C. the streak culture is cream, raised, finely wrinkled, with a dull surface.

Dalmau plate cultures on corn meal agar: Growth poor, off-white. Pseudomycelium is present, sparse and short. True, septate mycelium is rarely present. Single or paried ovoid to globose blastospores are formed terminally or pleurally, sometimes in groups.

Fermentation: Negative on glucose, galactose, sucrose, maltose, trehalose and lactose.

| Assimilation of carbon compounds: (basal medium plus leucine ethyl ester and uracil) | | | | | |
|---|---|---|---|---|---|
| Glucose | weak | Soluble starch | − | Ribitol | − |
| Galactose | − | | | Galactitol | − |
| L-Sorbose | − | D-Xylose | − | D-Mannitol | + |
| Sucrose | − | L-Arabinose | − | D-Glucitol | − to weak |
| Maltose | − | D-Arabinose | − | Salicin | − |
| Cellobiose | − | D-Ribose | weak | DL-Lactic acid | weak |
| Trehalose | − | L-Rhamnose | − | alpha-Methyl-D-Glucoside | − |
| Lactose | − | Ethanol | weak | | |
| Melibiose | − | Glycerol | − to weak | Succinic acid | − to weak |
| Raffinose | − | Erythritol | + | Citric acid | − |
| Melezitose | − | | | Inositol | − |

Assimilation of potassum nitrate (plus leucine ethyl ester and uracil): Negative.

Growth in vitamin-free medium (plus leucine ethyl ester and uracil): Negative.

Vitamin stimulating growth: Thiamine in broth with leucine ethyl ester and uracil stimulates weak or no growth.

Sodium chloride tolerance: 11%–12%.

Maximum temperature of growth: Between 37° C. and 45° C.

Y. lipolytica PC-30827 contains the rarely reverting mutation leu2-35. The Y. lipolytica LEU2 gene codes for the enzyme beta-isopropylmalate dehydrogenase (EC1.1.1.85) and is coded for by the leuB gene in E. coli and the LEU2 gene in S. cerevisiae.

Insertion of pLD25 into each of E. coli JC-355 and Y. lipolytica ATCC 20688 gave transformants comprising pLD25 in E. coli JC-355 and in Y. lipolytica ATCC 20688, respectively. They are identified in the culture collection of Pfizer Inc. as F.D. 27534 and F.D. 27533, respectively. Each of the transformants has been deposited in the ATCC under the conditions of access thereto as set forth above, and been assigned the accession number ATCC 39464 and ATCC 20687, respectively.

Chromosomal DNA from Y. lipolytica strain NRRL Y-1094, a wild-type strain (i.e., a strain customarily used by those skilled in the art for microbiological processes) was obtained by the method of Hereford et al., Cell, 18, 1261–1271 (1979).

The novel plasmid pLD25 of this invention was constructed by ligation of linearized pBR322 with a partial Sau3A digest of Y. lipolytica chromosomal DNA by means of T4 ligase. The pBR322 was isolated by centrifugation in CsCl-ethidium bromide gradients to separate covalently closed supercoiled pBR322 from bacterial DNA. The pBR322 was linearized by cleavage within the tetracycline resistance gene (Tc®) by digestion with the restriction endonuclease BamH1 resulting in a linear fragment having cohesive (sticky) ends and leaving ampicillin resistance (Amp®) as the phenotypic trait. Gel (agarose) electrophoresis of the vector showed it to be substantially free of bccterial DNA. The linearized pBR322 thus-produced is then desirably treated with alkaline phosphatase to prevent subsequent self-ligation; i.e., recircularization and dimer formation of the vector DNA.

The second component of pLD25 is obtained by subjecting the chromosomal DNA of Y. lipolytica strain NRRL Y-1094, a wild-type strain, to partial digestion with restriction endonuclease Sau3A which generates cohesive ended, nearly random fragments complementary to those of the BamH1 cleavage of pBR322. DNA in the range of 4–10 kb, harvested from agarose gels, was purified by known procedures prior to ligation with BamHI-cut, alkaline phosphatase treated vector pBR322.

The size of the DNA fragments is not critical to the process of this invention. The critical aspect as regards said DNA fragments is that they contain all or a sufficient part of the detectable marker, e.g. the LEU2 gene. Additionally, they must contain cohesive ends complimentary to those generated by the restriction endonuclease cleavage of the E. coli plasmid, in this case, pBR322.

The vector DNA and the partial Sau3A digest of Y. lipolytica chromosomal DNA are ligated by means of T4 ligase in the presence of adenosine triphosphate (ATP) as cofactor.

The ligation mixture is first transformed into E. coli MC 1061 (Casadaban et al., J. Mol. Biol. 138, 179–207, 1980), a strain of E. coli which gives a very high transformation frequency and is hsdR⁻ hsdM⁺, thus affording a Y. lipolytica gene library in said E. coli. The total potentially different ampicillin-resistant transformants of E. coli MC 1061 were grown together on ampicillin plus L agar plates and harvested. The harvested culture was grown in one liter o ampicillin containing medium. The mixed plasmids were isolated by standard methodology to produce a gene library. A sample of said library was transformed into E. coli JC-355. Transformants were selected on the basis of ampicillin resistance. These transformants were then replica plated to synthetic media lacking leucine. Alternatively, the transformation mixture could be directly plated on synthetic media lacking leucine and containing ampicillin. Several transformants thus selected were leucine prototrophic. The plasmid in said transformants is isolated by standard methods and referred to as pLD25.

Plasmid minipreparations made from the rare leucine prototrophic transformants and analyzed by digestion with HindIII and SalI are found to contain the expected 3.7 kb fragment from pBR322 and 2 large fragments indicating an insert size of approximately 6.6 kb. Additionally, a small fragment (from the SalI site of pBR322 to the nearer SalI site of the insert see FIG. 3) was found. Comparison of Southern blot hybridizations (Southern, J. Mol. Biol. 98, 503–517, 1975) of plasmid pLD25 with hybridizations of EcoRI digested chromosomal DNA of Y. lipolytica showed the 3 fragments internal to the cloned insert to be identical in the chromosomal DNA.

Transformants of Y. lipolytica with intact pLD25 and with KpnI-cut pLD25 were tested to determine whether they contain integrated or independently replicating pLD25 (the LEU2-containing plasmid). Chromosomal DNA was prepared from the leucine prototrophic transformants and the parent Y. lipolytica ATCC 20688. The DNA samples were cleaved with HindIII, run on 0.5% agarose gel, and analyzed by the Southern blot technique using radioactive pBR322 to measure the presence of plasmid pLD25 in the samples. No homology between the parent Y. lipolytica strain and the probe was observed. Since there is one HindIII site in pLD25 (within the pBR322 segment), and none in the Y. lipolytica segment, one band of pLD25 size (approximately 11 kb) would be seen if pLD25 was replicating independently in the transformants. The absence of such a band leads to the conclusion that the transformants are all integrants. Circular, linearized and gapped-linearized plasmids can transform Y. lipolytica by recombination with homologous chromosomal sequences. However, the transformants frequency was much higher in the KpnI-cut plasmid-treated cells than in the intact plasmid-treated cells further indicating that integrative transformation as described by Orr-Weaver et al. for S. cerevisiae (Proc. Natl. Acad. Sci., 78, 6354–6358, 1981) occurred in Y. lipolytica as well. The Southern blots mentioned above show that the structure of the integrate transformants derived from linear molecules behaves identically to that of transformants derived from circular molecules (i.e. plasmids). Further Southern blot experiments have shown that some of the rare transformants resulting from intact-plasmid treatments lack pBR322-hybridizable material and probably arose from gene conversion or double recombination events.

The usefulness of the herein described transformation system is demonstrated in the shuttling of the integrating plasmids described in said transformation system from *Y. lipolytica* to *E. coli* to complete the cycle. Further, the integrative shuttle vectors enable cloning of desired *Y. lipolytica* genes by construction of gene libraries followed by selection or screening in a *Y. lipolytica* recipient.

EXPERIMENTAL

Materials and Methods

Most restriction enzymes, including, BamHI, SalI, BglII, HindIII and Sau3A were obtained from New England Biolabs (NEB) as was T4 DNA ligase and *E. coli* polymerase I. ApaI was obtained from Boehringer-Mannheim. All enzymes were used according to the conditions for their use described by the respective manufacturers. SalI was also obtained from Bethesda Research Laboratories (BRL), as was the bacterial alkaline phosphatase, KpnI and XhoI. The bacterial alkaline phosphatase was used at approximately 100 units per microgram of linearized plasmid DNA at 65° C. in BamHI assay buffer for two hours. Restriction digests were analyzed by electrophoresis in submerged 0.8% agarose gels using Tris-Borate-EDTA buffer (Maniatis et al., "Molecular Cloning", Cold Spring Harbor Laboratory, N.Y., 1982).

Media

*E. coli* rich medium was L broth containing, per liter, 10 g Bacto-tryptone, 5 g Bacto-yeast extract, and 5 g NaCl, adjusted to pH 7.5. *E. coli* minimal medium was 56 salts with 0.33% dextrose (Low, J. Bacteriol. 113, 798–812, 1973). Amino acids or bases were supplemented to 50 µg/ml where needed. Bacteria were grown at 37° C.

Yeast rich medium was YPD, containing 1% Bacto-yeast extract, 2% Bacto-Peptone, and 2% dextrose. Yeast minimal medium, SD, contained 0.67% Bacto-yeast nitrogen base without amino acids and 2% dextrose. Synthetic complete medium contained 870 mg/l of powdered stock supplements made by grinding the following together in a mortar and pestle: 2 g each of adenine sulfate, uracil, tryptophan, histidine-HCl, arginine-HCl and methionine, 3 g tyrosine, 6 g leucine, 5 g phenylalanine, 20 g threonine, 3 g lysine. For nutritional testing or selection, the appropriate ingredient was left out of complete medium. *Y. lipolytica* was grown at 28° C.

Isolation of *Y. lipolytica* Chromosomal DNA a. Cloning Quality DNA. The wild type strain NRRL Y-1094 was grown at 28° C. to $1-2 \times 10^8$ cells per ml in $4 \times 300$ ml of YPD in shaking Fernbach flasks, following inoculation with 15 microliters from a fresh stationary phase culture. All of the following manipulations of the cells were performed at 28° C. or room temperature. The cells were harvested by centrifugation, washed in 50 ml 1M NaCl, and spun down again. Then, a 15 minute "pre-spheroplasting" incubation in 50 ml of 0.2M tris(hydroxymethyl)aminomethane-HCl (Tris-HCl) pH 8.5, 0.02M ethylenediaminetetracetic acid (EDTA), 1M NaCl, and 0.1M 2-mercaptoethanol was followed by centrifugal harvesting. The cell pellet was resuspended in 40 ml of 1M NaCl containing 1 mg per ml Zymolyase 5000 (from Kirin Breweries, Japan) and incubated for 45 minutes. At this time greater than 90% of the cells were converted to spheroplasts as detected microscopically by cell lysis upon dilution into water.

The spheroplasts were spun down and resuspended in 4 tubes in a total of 16 ml 1M NaCl. Forty ml of lysis buffer [50 mM Tris pH 6.8, 100 mM NaCl, 100 mM EDTA, 0.5% sodium dodecylsulfate (SDS)] containing 0.1 mg/ml proteinase K was added and the lysate incubated at 37° for 1.5 hours. The lysate was extracted with an equal volume of phenol:chloroform (1:1). Following centrifugation at 9000 rpm to separate the phases, the aqueous phase was again extracted with phenol-chloroform. The final aqueous phase was combined with two volumes of ethanol to produce large precipitates of DNA. The liquid was poured off and the pellet rinsed with 70% and 100% ethanol before vacuum drying. The dried pellet was redissolved in 8 ml TE (10 mM Tris-HCl pH 8, 1 mM EDTA) at 65° C. followed by RNAse digestion with 300 microliters of RNAse A (1 mg/ml, boiled 5 minutes) for 1 hour at 37° C. The material was extracted twice with phenol-chloroform and ethanol precipitated as before. The final precipitate was rinsed with ether before vacuum drying.

The DNA pellet was redissolved in TE as before and 2 ml $100 \times$ TE was added followed by water to 29.04 g. The solution was added to 37.67 g of CsCl, transferred into centrifuge tubes, and spun for 17 hours at 40,000 rpm at 15° C. in a Beckman L8-70 ultracentrifuge using a VTi 50 rotor. The gradient was harvested by dripping fractions containing approximately 1.25 ml from the bottom of the tube following puncture with a needle. The fractions were assayed for DNA by running samples on an agarose gel containing 0.5 mcg/ml ethidium bromide, and fractions 16, 17, and 18 (out of 26) were saved. These DNA-containing fractions were pooled, dialyzed against four changes of $1 \times$ TE and ethanol precipitated. The DNA was redissolved in 0.6 ml $1 \times$ TE and the preparation was estimated, by absorbance at 260 nm, to contain 129 micrograms of DNA.

b. DNA for Southern Blots. We found that the SDS spheroplast lysis and potassium acetate treatment from the *S. cerevisiae* mini-prep method (compiled in Sherman et al., "Methods in Yeast Genetics", Cold Spring Harbor Laboratory, N.Y., 1981) was convenient for obtaining *Y. lipolytica* DNA.

Preparation of Plasmid DNA. Bacterial plasmid DNA was prepared by the rapid boiling method of Holmes et al., Anal. Biochem. 114, 193–197 (1981). Subsequent centrifugation in CsCl-ethidium bromide gradients were performed only for large scale preparations. DNA preparations were stored at 4° C. in sterile TE buffer.

*E. coli* Transformation. The $CaCl_2$ method of Dagert et al., Gene 6, 23–28 (1979) was used. Both overnight $CaCl_2$-treated and briefly treated cells were used in transformations.

Southern Blot Experiments. DNA transferred to nitrocellulose (Southern 1975) was hybridized to $^{32}$P-labelled "nick translated" probes in $6 \times$ SCP buffer ($20 \times$ SCP stock contains 2.0 M NaCl, 0.6 M $Na_2HPO_4$, and 0.2 M EDTA pH 6.2), 1% sacrosyl, with 40 µg/ml denatured calf thymus or *E. coli* DNA. The nick translation method of Maniatis et al. (loc. cit.) was used with *E. coli* polymerase I.

Preparation of Sau3A Partial Digests of *Y. lipolytica* DNA. Approximately 15 micrograms of this DNA was partially digested with the restriction enzyme Sau3A (New England Biolabs) in each of four tubes using 0.05, 0.1, 0.2 and 0.4 enzyme units per microgram of DNA for 0.5 hour at 37° C. following the suppliers protocol. The reactions were stopped by heating at 65° C. for 10 minutes then loaded onto 0.8% preparative agarose gels. DNA in the size range of 4 to 10 kilobases (compared to HindIII-cut lambda size standards from Bethesda Research Labs) was harvested from the gels, electroeluted, purified on DE52 columns (Yang et al., Methods in Enzymology, 68, 176, 1979) and ethanol precipitated before ligation with BamHIcut, alkaline phosphatase-treated, vector pBR322.

Construction of a Gene Library of *Y. lipolytica* in Vector pBR322. The ligation mix containing approximately 1 μg of DNA was used to transform *E. coli* strain MC1061 (Casadaban et al., J. Mol. Biol. 138, 179–207, 1980) to create a *Y. lipolytica* gene library. The transformation mixture gave approximately $1.4 \times 10^4$ colonies on 10 μg/ml ampicillin plus L agar plates. Fifty colonies were placed on a single plate and replica plated to test resistance to 5 μg/ml tetracycline. Forty-four (88%) were sensitive indicating they most likely contained an insert in the BamHI site to interrupt the tet® gene of pBR322. Mini-scale plasmid preparations from 18 randomly chosen amp® colonies were examined by restriction enzyme digestion with HindIII and SalI double digests and BamHI digests. Ten of the plasmids had inserts, averaging approximately 7 kilobases in size.

Forty-eight ampicillin plates containing approximately $1.4 \times 10^4$ *E. coli* transformant colonies were replica plated to LB plus 10 μg/ml ampicillin. The replicas were washed with 5 ml 0.85% NaCl each. The pooled cells were pelleted by centrifugation and resuspended in 11 ml LB and 2.5 ml 80% glycerol. Two cultures with 1 L of LB and 10 μg/ml ampicillin in Fernbach flasks were set up with 4 ml of the pooled bacteria each, and the remaining bacteria were stored at −70° C. The cultures were used to prepare the plasmid DNA that was designated as our *Y. lipolytica* gene library of Sau3A partial digest fragments in pBR322.

Screening the Gene Library in *E. coli* Mutants. Several *E. coli* strains mutant for didfferent genetic markers were transformed with the gene library. In order to obtain genetic complementation, two major factors are necessary: (1), the corresponding *Y. lipolytica* gene must be contained intact on at least one of the plasmids in our library; and (2), the *Y. lipolytica* gene must function to a sufficient extent in *E. coli* cells. The library was screened both by direct selection for each marker on the appropriate medium and also by initial selection for ampicillin resistance followed by replica plating onto selective medium. For each genetic marker examined, at least $10^5$ transformants were examined. Strain JC355 was used to successfully clone the LEU2 gene.

Any *E. coli* colonies that grew on selective media were further examined by a "re-transformation" test. For this test, plasmid was prepared from a 5 ml culture of the strain that grew on selective media. The plasmid mini prep was then used to transform that parent, mutant *E. coli* strain. The presence of many ampicillin-resistant transformants but few or no colonies on selective media, led to the conclusion the original colony did not contain the desired *Y. lipolytica* gene and most likely grew because of mutation to prototrophy. If all of the ampicillin-resistant colonies also grew on selective media for the gene being tested, it was concluded that the plasmid obtained from the original colony contained an insert that complemented the *E. coli* mutation. A total of 7 leucine-independent transformants of JC355 (leuB6) that contained the idetitcal insert into pBR322 were found. Plasmid mini-preparations from two of these colonies gave 100% (37/37 and 31/31) ampicillin-resistant leucine prototrophic transformants in the re-transformation test. The plasmid was designated pLD25.

Figure 2:
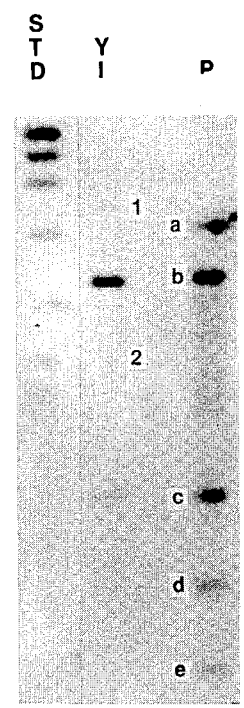

Verification that the *E. coli* leuB6-Complementing DNA came from *Y. lipolytica*. To verify that the insert DNA from pLD25 came from *Y. lipolytica*, a Southern (1975) blot experiment was performed. A new preparation of *Y. lipolytica* total DNA was made, omitting the final CsCl gradient step. The EcoRI digestion pattern of the *Y. lipolytica* DNA revealed identity with three bands internal to the insert in pLD25 (FIG. 2).

Figure 3:
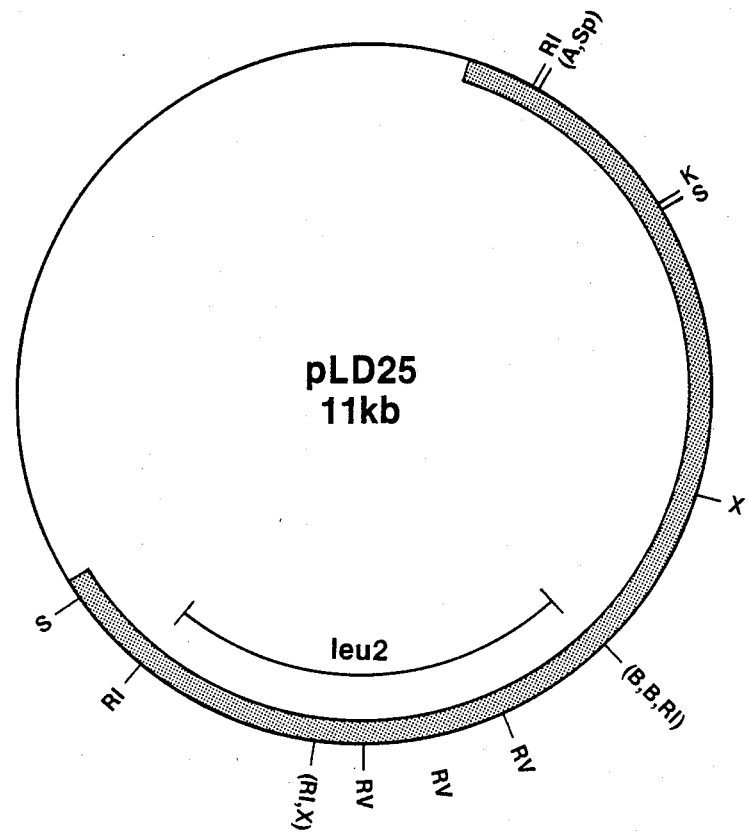

Further Characterization of the Insert in pLD25. A partial restriction map of pLD25 was derived using several common enzymes (FIG. 3). The total amount of *Y. lipolytica* DNA contained in the plasmid was estimated at approximately 6.6 kb.

Transformation Protocol. A modification of the lithium acetate method (Ito et al., J. Bacteriol. 153, 163–168, 1983) with the sonicated carrier DNA addition used for *S. cerevisiae* transformation was adapted for *Y. lipolytica* transformation. Late log phase cultures $3$–$10 \times 10^7$ cells/ml usually gave more transformants than log phase ($1 \times 10^7$ cells/ml) cultures. Fifty ml YPD cultures were pelleted and then resuspended in 10 ml of 10 mM Tris, 1 mM EDTA pH 7.5. They were repelleted and resuspended in 2–3 volumes of the above buffer plus 0.1 M lithium acetate and mixed gently on a New Brunswick roller drum at 28° C. for 1 hour. The Li-treated cells were separated into multiple transformation tubes containing between 0.1 and 1.0 ml of cells, 1 μg of transforming plasmid and 50 μg sonicated heterologous carrier DNA (the size range appeared to be 0.5–9 kb on an agarose gel). The transformation tubes were left at 28° C. for 30 minutes and then 7 volumes of PEG reagent (40% polyethylene glycol 4000, 0.1 M LiAc, 10 mM Tris, 1 mM EDTA pH 7.5—filter sterilized) was added. After an additional 1 hr at 28° C., the heat pulse (usually 37° C. for 5 minutes) was used. The cells were finally spun down at 3000 rpm for 2 minutes, resuspended in water, and plated on appropriate media.

Construction of pLD28

Figure 6:
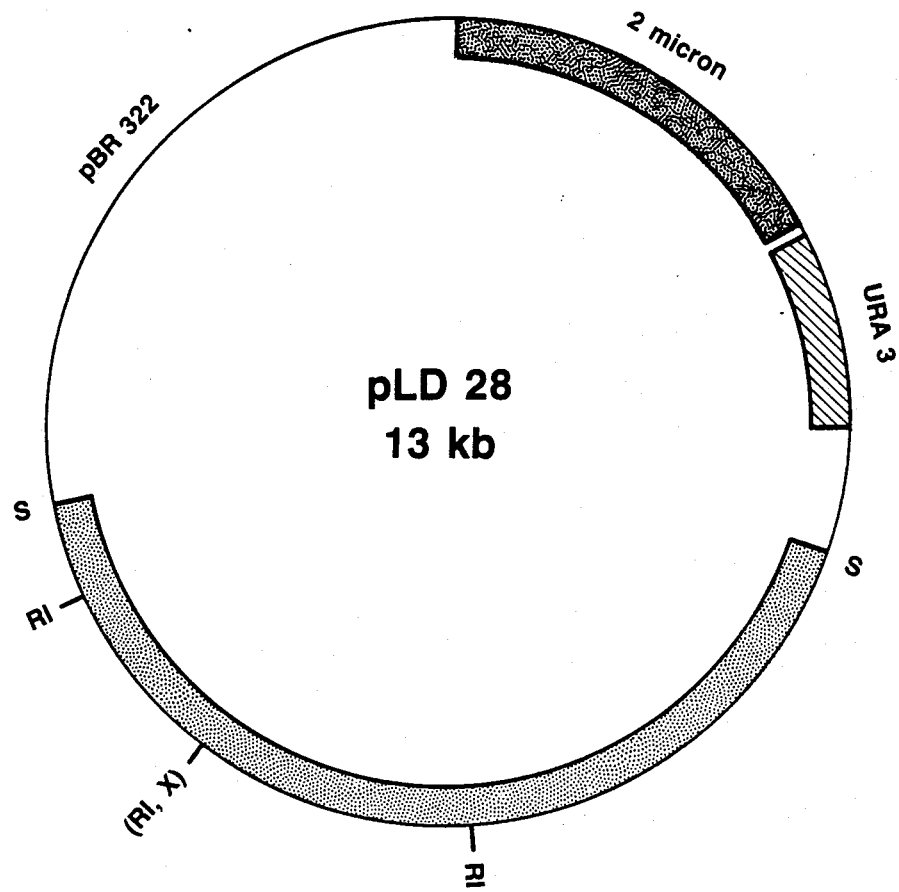

A mixture of 2 μg each of pLD25 and YEp24 (ATCC 37051) was incubated at 37° C. with 6.25 units of SalI in 50 μl of SalI buffer for 1.5 hours. The digest was then extracted with an equal volume of phenol followed by three extractions with ether (1.5 ml.). The DNA was precipitated by addition of sufficient sodium chloride and absolute ethanol to give 0.1M sodium chloride and 70% ethanol concentration. The DNA was removed and dissolved in an equal volume of TE buffer. Ten μl of the DNA solution was then treated with T4 DNA ligase in 20 μl reaction volume for one hour at 14° C. Selection for the desired recombinant plasmid was carried out by transforming *E. coli* DB 6507 according to the following procedures. The transformation mixture was plated on 11 *E. coli* synthetic media plates containing threonine, proline and leucine but lacking uracil. More than 100 colonies per plate were obtained. The resulting transformants were replica plated to leucine-deficient plates to test for the presence of the *Y. lipolytica* LEU2 gene on each plasmid. Those colonies that grew slowly without added leucine were streaked for single colonies on ampicillin plates and tested for tetracycline sensitivity. Twenty-four colonies that were ampicillin resistant, tetracycline sensitive were used for mini-plasmid preparations. The plasmid DNA preparations were analyzed by SalI digestion for the two expected bands (7.5 kb from YEp24 and 5.3 kb from LEU2) and by EcoRI digestion for the 5 expected bands (FIG. 6). Two plasmids had the appropriate pattern. The first plasmid was saved and designated pLD28.

Construction of pLD40/plasmid having smaller segment of the LEU2 gene than either of pLD25 or pLD28

A partial EcoRI digest of pLD25 was carried out by treating approximately 25 micrograms of pLD25 with 20 units of restriction enzyme in 200 microliters and removing aliquots at 9, 12, 15, 18 and 21 minutes. At each timepoint, 20% of the total volume was placed in gel sample buffer containing 33 mM EDTA (after dilution) to stop the reaction. The timepoints were run on a gel and the desired band (migrating slightly slower than the 2.3 kb lambda HindIII size-standard) was excised with a razor blade. The band was electroeluted in a dialysis bag and purified on a mini-column (Schleicher and Schuell Elutip-D), as directed by the supplier. The vector used to clone the LEU2-containing band was EcoRI-digested, bacterial alkaline phosphatase-treated pBR322. The vector and insert DNA were combined with T4 DNA ligase and the resulting mixture used to transform $E.$ $coli$ strain MC1061 to ampicillin-resistance. Plasmid mini-preparations were examined by digestion with EcoRI restriction endonuclease. Four of the first 34 preparations contained the desired insert. To test the orientation of the inserts in each plasmid, HindIII and XhoI double digests were done. Three had the orientation of pLD40 (FIG. 7), and one the reverse orientation. It was named pLD41. These two plasmids were transformed into $E.$ $coli$ JC355 (after large scale preparations were made in MC1061) to test for the expression of the $Y.$ $lipolytica$ LEU2 gene. Surprisingly, the transforaant containing pLD40 gave excellent growth on media lacking leucine (better than transformants containing pLD25 or pLD28) but the transformant containing pLD41 did not grow without added leucine. Bacterial complete media for this experiment consisted of 56/2 plus vitamin B1, glucose, histidine, arginine, methionine, leucine and 20 micrograms/ml ampicillin. It was concluded that transcription of the LEU2 gene in pLD40 was being promoted by the counter-clockwise promoter P1 described by D. Stuber and H. Bujard (1981, Proc. Natl. Acad. Sci., 78:167-171). It is possible that the lower level bacterial expression of the $Y.$ $lipolytica$ LEU2 gene in pLD25 and pLD28 (compared to pLD40) results from a segment of $Y.$ $lipolytica$ DNA acting as a weak bacterial promoter.

Transformation of a $Y.$ $lipolytica$ leu2 Mutant with pLD25. $Y$ $lipolytica$ strain PC-30827 (MATA leu2-35 ura3-11) ATCC 20688 constructed by J. R. DeZeeuw was used as a recipient for the LEU2 gene cloned in pLD25. It was found that cultures in later stages of growth gave more transformants than early log phase cells. This finding held true even when approximately equal numbers of early vs. late log phase cells were treated with DNA and plated on leucine-deficient plates. Plasmids that had been linearized by either a cut at a unique restriction site or by leaving a small gap (BglII-cut) in the $Y.$ $lipolytica$ DNA gave many more transformants than intact pLD25 or plasmid linearized by cutting at the HindIII restriction site in pBR322. These latter results are similar to the integrative transformation system in $S.$ $cerevisiae$ developed by Orr-Weaver et al., loc. cit. The addition of sonicated $E.$ $coli$ DNA to the pLD25 used in transformation gave more transformants than when either large molecular weight or no carrier DNA was added. Minor variations in the duration and temperature of the heat shock following incubation of the cells with DNA and polyethylene glycol appears to have only a small effect on the yield of transformants.

Stability of the Transformants. A colony of the transformant comprising pLD25 in $Y.$ $lipolytica$ ATCC 20687, designated herein as DL10, was streaked out on a YPD plate for single colonies following growth non-selectively on a YPD plate. The resulting YPD culture plate was replicated onto leucine-deficient synthetic medium. All of the approximately 50 well-separated colonies were leucine independent, demonstrating stability of the transformants.

Figure 4:
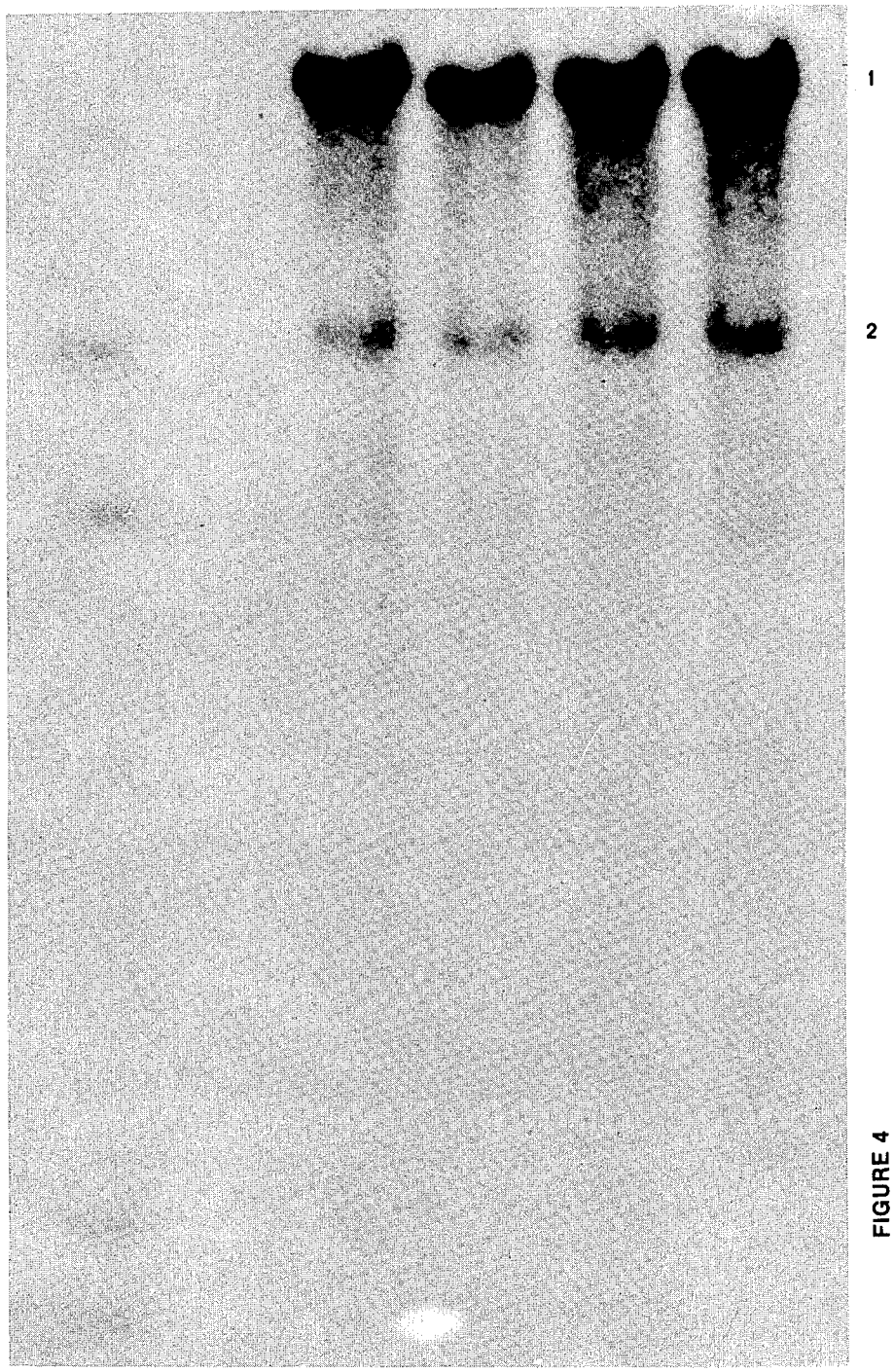

Southern Blot to Detect Integration of pLD25. The $Y.$ $lipolytica$ transformants were stable and the transformation frequency was greatly increased by linearization of the donor plasmid DNA. This indicated the transformants resulted from integration of the plasmid into chromosomal DNA at the site homologous to the ends of the donor DNA as found in the $S.$ $cerevisiae$ system by Orr-Weaver et al., loc. cit. A Southern blot experiment (FIG. 4) of HindIII digests of $Y.$ $lipolytica$ DNA showed the same two bands of homology to pBR322 in transformants resulting from either intact or linearized plasmid. The observation that one band was larger than the 23 kilobase lambda size standard is evidence of integration of the plasmid into chromosomal DNA.

Cloning of $Y.$ $lipolytica$ H1S1 Gene

Gene Library Construction. The vector YEp24 (Botstein et al., Gene 8, 17-24, 1979) was digested with BamHI and treated with alkaline phosphatase as described previously for pBR322. The insert DNA used in the ligation reaction was a complete BamHI digest of $Y.$ $lipolytica$ chromosomal DNA obtained from $Y.$ $lipolytica$ NRRL Y-1094 as described above. The chromosomal DNA digest was not size-fractionated before ligation, only phenol extracted. A total of approximately 27,000 ampicillin-resistant transformant colonies of $E.$ $coli$ strain MC 1061 were obtained using the ligation products. The plasmid DNA obtained from cultures of these pooled transformant colonies was designated as the library of BamHI fragments of $Y.$ $lipolytica$ in YEp24. The insert frequency was estimated as 95 percent (19/20 transformants were tetracycline-sensitive) and the average insert size was 4.2 kb.

Isolation of the HIS1 Gene. The BamHI library was used to transform many different $E.$ $coli$ auxotrophs in an attempt to find $Y.$ $lipolytica$ gene that would complement a mutant $E.$ $coli$ gene. Two transformant colonies of the $E.$ $coli$ hisG1 mutant AT2535 (obtained as #4517 $E.$ $coli$ Genetic Stock Center, Yale University) were isolated on synthetic medium lacking histidine and containing ampicillin. Both colonies contained the same plasmid pLD21, which consisted of an insert of approximately 4 kb into the vector. The retransformation test was positive with 419/419 ampicillin-resistant transformants of AT2535 with pLD21 scored as histidine-independent by replica plating. A Southern hybridization experiment showed that the BamHI insert in pLD21 as well as the two insert fragments generated by a BamHI plus EcoRI double digest, co-migrated with fragments of *Y. lipolytica* chromosomal DNA that had been similarly cut.

To test if other alleles of hisG could be complemented by pLD21, *E. coli* strain NK5526 (*E. coli* Genetic Stock Center #6416) which contains a Tn10 insertion into the HISG gene, was transformed with the plasmid. All ampicillin-resistant transformant colonies were capable of slow growth following replica plating to media without histidine as would be expected from the polarity effect of Tn10 on the downstream genes in the histidine operon. Direct selection for the transformants on defined media lacking histidine and containing ampicillin was not possible, presumably because of the strong polarity effect. Since the *Y. lipolytica* DNA insertion in pLD21 was capable of complementing hisG mutations in *E. coli*, we concluded that it contained the *Y. lipolytica* HIS1 gene in a form that functioned in *E. coli*.

Figure 5:
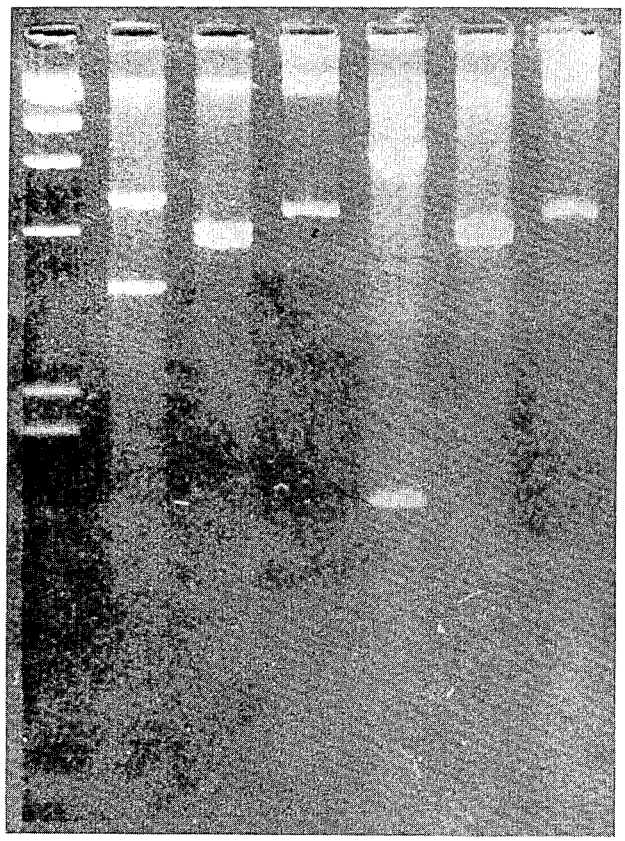

The Effect of Orientation on Expression. To test if the *Y. lipolytica* DNA insert was functioning independently of the vector YEp24, the BamHI piece was subcloned into pBR322. Inserts in both orientations were determined by the EcoRI digest pattern (FIG. 5). Plasmid pLD23, the plasmid with the EcoRI site of the insert further from the EcoRI site of pBR322, complemented the two hisG *E. coli* mutants used previously, whereas pLD24, the other orientation failed to complement the mutations. Thus, a sequence on the plasmid is needed for efficient expression of the *Y. lipolytica* HIS1 gene in this *E. coli* system. It is believed the tet ® promoter of pBR322 is the necessary component.

Transformation with Extended Segments of Chromosomal DNA. The approximately 5.3 or 5.4 kb long SalI piece of *Y. lipolytica* DNA containing the LEU2 gene (gel purified from a plasmid digest) was found to be capable of transforming the *Y. lipolytica* leu2 mutant recipient to prototrophy at a high frequency (greater than 1000 transformants per microgram). This integration event represents a different kind of recombination from transformation with a linearized plasmid. It affords the opportunity of inserting a desired sequence within a region of *Y. lipolytica* DNA and integrating the desired sequence without also integrating the bacterial vector into the host. This type of system has been developed in *S. cerevisiae* by R. Rothstein, Methods in Enzymology 101:202 (1983). Preparations of *Y. lipolytica* chromosomal DNA, both large molecular weight and lightly sheared were also used to obtain LEU2ttransformants.

Cloning of the URA3 Gene

The first step comprised construction of a gene library of Sau3A partial digests of *Y. lipolytica* DNA in the BamHI site of pLD40 according to the procedure described above for construction of a gene library in pBR322.

To obtain a high frequency of transformation and also to target the molecules in the library to integrate at the LEU2 locus, the library DNA was digested with the enzyme ApaI which makes one cut in the LEU2 region of the parent vector pLD40. (Since it was not known whether the unknown URA3 gene itself contained an ApaI site, a partial ApaI digest of a sample of the library DNA was also carried out to assure that some of the molecules so produced would be cleaved only at a single site. However, the partial digest was not necessary).

Transformation of a *Y. lipolytica* URA3 mutant with the pLD40 library

A 50 ml. culture of *Y. lipolytica* strain PC 30827 (ATCC 20688), the recipient, in YPD broth was grown to an OD at 600 nm of 4.9. This corresponded to a packed volume of 0.9 ml of cells following the wash step in pH 7.5 TE buffer as in the above-described transformation protocol. The cells were then suspended in twice their volume of lithium acetate in TE, mixed gently on a roller drum at 30° C. for one hour and then divided into three transformation tubes. Each tube (15 ml. Corning polystyrene centrifuge tubes) received 0.9 ml. of cell suspension, 300 µg (100 µl) of sonicated heterologous *E. coli* carrier DNA and 6 µg of ApaI-treated library DNA. The transformation tubes were incubated at 30° C. for 30 minutes and then mixed with 7 ml. of PEG reagent (described above) and incubated for an additional hour. The tubes were then subjected to a heat shock of 37° C. for ten minutes after which the cells were spun down at 3000 rpm for 2 minutes. The cells from each tube were resuspended in 0.6 ml. of sterile water and plated on 12 plates of leucine deficient synthetic complete media.

After 3 days a total of approximately 10,000 colonies grew on the leucine-deficient media. The negative control plate done in parallel to the transformation experiment (no DNA was used on these cells that were otherwise treated identically to the transformed cells) contained no growing leucine-independent colonies.

The 36 transformation plates were replica plated to uracil-deficient synthetic media. Only one colony that was uracil-independent was found the next day. This colony was further processed to recover the URA3 gene as described below. A second transformation experiment was done to determine whether direct selection for uracil-independence rather than a first selection for cells that had received a plasmid (i.e. leucine-independence) followed by screening for the desired trait was possible. This second experiment was similar to the first but gave a higher transformation frequency of between 5,000 and 10,000 transformants per microgram of transforming DNA. Three additional URA3 transformants were obtained in this experiment by direct selection onto uracil-deficient medium and one more by leucine-selection followed by screening.

Recovery of the URA3 Containing Plasmid pLD55

Figure 8:
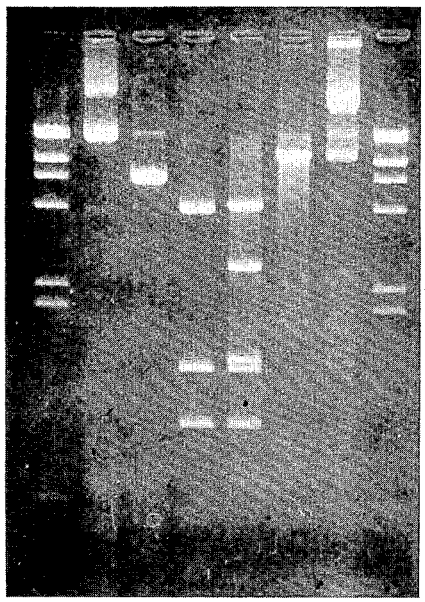

A 50 ml. YPD culture of the first uracil-independent transformant was grown overnight and harvested for DNA preparation using the phenol-chloroform and protease method as described previously. Approximately 3 micrograms (7%) of this chromosomal DNA preparation were digested to completion with the enzyme ApaI, followed by extractions with phenol, phenol-chloroform and chloroform-isoamyl alcohol and then ethanol precipitation. This DNA was ligated with T4 DNA ligase in a total volume of 80 microliters. Ten microliters of this reaction was used to transform 100 microliters of competent *E. coli* strain MC1061 to ampicillin-resistance. *E. coli* mini-plasmid preparations were made from 9 transformants and used for a restriction analysis. All 7 preparations that gave cleavable DNA contained identical restriction patterns with the enzymes ApaI and EcoRI (FIG. 8). The 2 preparations that presumably were not clean enough to allow enzyme digestion had identically-migrating supercoiled plasmids as the other 7. The plasmid recovered contained the two EcoRI bands characteristic of the LEU2 insert in pLD40 in addition to three other bands. To the accuracy of the gel shown (approx. 0.5 to 1 kb) the URA3-containing insert in pLD40 lacked an ApaI site and contained 2 EcoRI sites.

To verify that the plasmid did, in fact, contain the URA3 gene, a retransformation experiment was run. The mini-prep Apa I digest was used to transform the *Y. lipolytica* recipient. Part of this transformation mixture was plated on uracil-deficient media and part on leucine-deficient media. Plates with approximately 100 transformants on each type of media were chosen for replica plating to the other medium. All of the leucine-selected colonies were also uracil-independent. Surprisingly only approximately one-half of the colonies selected on the uracil-deficient media were also leucine independent. This latter result can be explained by certain hypotheses about degradation and repair of the transforming DNA in the targetted region (as in Orr-Weaver, et al., Methods in Enzymology 101:228 [1983]). Since all of the leucine-independent transformants were also uracil-independent, it is concluded that integration of the plasmid at the LEU2 region complemented the ura3 mutation and that the plasmid, designated pLD55 contained the URA3 gene of *Y. lipolytica*.

Demonstration of Shuttling

DNA was prepared from the *Y. lipolytica* transformant with pLD25 (ATCC 20687) by the phenol-chloroform/protease method described above, but without subsequent application of the cesium chloride gradient.

A few micrograms of the DNA thus isolated was digested with the enzyme KpnI (the same enzyme used to make the transformant), phenol extracted, purified on a Schleicher and Schuell Elutip-D minicolumn (following the manufacturer's directions) and then ligated using T4 DNA ligase. Ligations at both medium (more than 50 micrograms DNA per ml) and low (less than 10 micrograms/ml) concentrations were successful in the ensuing bacterial transformation. The ligation mixtures were used to transform *E. coli* strain MC1061 for ampicillin resistance as described previously. More than 10 *E. coli* transformants were collected and mini-plasmid preparations were done. The vast majority of these contained plasmids identical by restriction pattern to pLD25. A few contained apparent inserts of different pieces of DNA into the KpnI site of pLD25. Presumably these extra pieces were different KpnI fragments of *Y. lipolytica* DNA that became inserted into the linearized vector during the ligation.

A second example involves plasmid pLD28 and demonstrates the genetic functional differences between *Y. lipolytica* and *S. cerevisiae. Y. lipolytica* strain ATCC 20688 was transformed with BglII-cut pLD28 to yield strain DL11, which was selected on leucine-deficient synthetic medium. When replica plated to uracil-deficient synthetic medium, no growth was detected suggesting (since enzyme assay tests indicate that the *Y. lipolytica* URA3 gene codes for the same enzyme as the *S. cerevisiae* URA3 gene) that the *S. cerevisiae* gene did not complement the corresponding *Y. lipolytica* mutation. The plasmid was recovered from *Y. lipolytica* as above except the enzyme BglII was used so that the recovered plasmid lacked the small BglII fragment. To test if the *Y. lipolytica* LEU2 gene would function in *S. cerevisiae*, strain DB745 (leu2-3,112_ura3-52 ade1-100), constructed in D. Botstein's lab and widely used as a host for plasmids (see, for example, Guarente and Ptashne, 1981 Proc. Nat'l Acad Sci. USA 78; 2199, similar strains are available as ATCC 44773 and ATCC 44774) was transformed with pLD28, selecting on uracil-deficient medium. The *S. cerevisiae* transformants were replica-plated to leucine-deficient medium and were found to grow slowly without added leucine. It was possible to select directly for pLD28 in *S. cerevisiae* based on its ability to poorly complement leu2, although transformants arose 24-48 hours later on leucine-deficient plates than on uracil-deficient plates and a slightly lower transformation frequency was obtained. Thus, the *Y. lipolytica* LEU2 gene can function, albeit weakly, when on this multicopy plasmid in *S. cerevisiae*.

The generality of the herein-described method for obtaining *Y. lipolytica* genes from libraries by looking for said genes that will function in *Y. lipolytica* was further demonstrated by successful transformation of a *Y. lipolytica* protease gene and a *Y. lipolytica* adenine gene.

Using the previously described pLD40-based library and the shuttling system of this invention, a *Y. lipolytica* protease gene (XPR2) has been successfully cloned. The procedure used was similar to that described above for the cloning of URA3. XPR2 is the structural gene for the secreted alkaline protease (Sims and Ogrydziak, J. Bacteriol, 145, 404, 1981). Recipient strains of *Y. lipolytica* that included the genetic markers leu2, ade1 and xpr2 were constructed by standard genetic techniques (Ogrydziak et al., Mol. Gen. Genetics, 163, 229, 1978). The leu2 mutation is described herein and various xpr2 alleles and the ade1 allele are available from ATCC as numbers 46026-46028 and 46067-46070, deposited by Ogrydziak (see Sims and Ogrydziak, loc. cit).

The library was treated according to the ethidium bromide partial digest method of R. Parker, et al. (Proc. Natl. Acad. Sci. USA, 74, 851, 1977) using the enzyme BglII. To determine the appropriate amount of BglII enzyme, ethidium bromide, and DNA to use, a range of ethidium bromide concentrations from 0.005 to 1 microgram per microliter were used with approximately 1 microgram of library DNA in 10 microliters containing 4 enzyme units per tube. Incubation time was 1 hour at 37° C. The tube containing approximately 0.05 micrograms per microliter of ethidium bromide appeared to give much linearization of the plasmids in the library without creating any smaller fragments that would be indicative of more than one cut per molecule. This ratio of components was scaled-up to prepare library DNA for transformation purposes. This treatment of the library DNA avoids problems that would otherwise occur if both the targeted integration site (LEU2 region) and the desired unknown gene (XPR2) had sites for the enzyme being used for linearization (BglII). Transformants obtained from DNA thus treated could be integrants at either LEU2 or XPR2 regions of the genome. Using the same transformation method as previously, we obtained more than 80,000 colonies on leucine-deficient synthetic medium. These were replica-plated to skim milk indicator plates (D. Ogrydziak et al. Genetics 87, 621, 1977). Protease positive transformants were recognized by creation of a clearing zone on the skim milk plates.

Still further, the adenine gene of *Y. lipolytica* has been cloned by complementation. A double mutant recipient (leu2 ade1) was transformed as described above and leucine independent colonies replica-plated to media to select for ADE1. ADE1-containing plasmids are recovered from transformants and verified by retransformation.

We claim:

1. A process for integrative transformation of *Yarrowia lipolytica* which comprises introducing DNA into said *Y. lipolytica*, said DNA comprising a region of homology to chromosomal DNA of said *Y. lipolytica* sufficient to result in integrative transformation thereof and containing a detectable marker.

2. A process according to claim 1 wherein said DNA comprises a fragment of *Y. lipolytica* DNA, said DNA being detectable in said *Y. lipolytica*.

3. A process according to claim 2 wherein said *Y. lipolytica* is *Y. lipolytica* having the identifying characteristics of ATCC 20688.

4. A process according to claim 2 wherein said DNA contains the LEU2 gene of *Y. lipolytica*.

5. A process according to claim 3 wherein said DNA contains the LEU2 gene of *Y. lipolytica*.

6. A process according to claim 2 wherein said DNA is a vector containing a fragment of *Y. lipolytica* DNA.

7. A process according to claim 6 wherein said vector contains the LEU2 gene of *Y. lipolytica*.

8. A process according to claim 6 wherein said fragment is a portion of the LEU2 or the URA3 gene of *Y. lipolytica*.

9. A process according to claim 6 wherein said fragment contains a selectable marker which functions in *Y. lipolytica*.

10. A process according to claim 9 wherein said DNA is double stranded linear DNA capable of integration into *Y. lipolytica*.

11. A process according to claim 10 wherein said *Y. lipolytica* is *Y. lipolytica* having the identifying characteristics of ATCC 20688.

12. A process according to claim 9 wherein said *Y. lipolytica* is *Y. lipolytica* having the identifying characteristics of ATCC 20688.

13. A process according to claim 12 wherein said vector contains the LEU2 gene of *Y. lipolytica*.

14. A process according to claim 9 wherein said vector is an autonomously replicating *Escherichia coli* plasmid containing a *Y. lipolytica* DNA fragment, said fragment having a selectable marker selected from the group consisting of the HIS1, LEU2 and URA3 genes of *Y. lipolytica*, which gene functions physiologically in both *E. coli* and *Y. lipolytica*.

15. A process according to claim 14 wherein said DNA is double stranded linear DNA capable of integration into *Y. lipolytica*.

16. A process according to claim 9 wherein said vector contains the LEU2 gene of *Y. lipolytica*.

17. A process according to claim 9 wherein said *Y. lipolytica* has a mutation in the gene corresponding to said selectable marker.

18. A process according to claim 17 wherein said DNA is double stranded linear DNA capable of integration into *Y. lipolytica*.

19. A process according to claim 17 wherein said mutation is in the LEU2 or the URA3 gene of *Y. lipolytica*.

20. A process according to claim 19 wherein said mutation is in the LEU2 gene of *Y. lipolytica*.

21. A process according to claim 17 wherein said *Y. lipolytica* is *Y. lipolytica* having the identifying characteristics of ATCC 20688.

22. A process according to claim 14 wherein said vector contains the LEU2 gene of *Y. lipolytica*.

23. A process according to claim 17 wherein said *Y. lipolytica* is *Y. lipolytica* having the identifying characteristics of ATCC 20688.

24. A process according to claim 17 wherein said vector is an autonomously replicating *Escherichia coli* plasmid containing a *Y. lipolytica* DNA fragment, said fragment having a selectable marker selected from the group consisting of the HIS1, LEU2 and URA3 genes of *Y. lipolytica*, which gene functions physiologically in both *E. coli* and *Y. lipolytica*.

25. A process according to claim 24 wherein said mutation is in the LEU2 gene of *Y. lipolytica*.

26. A process according to claim 24 wherein said selectable marker is the LEU2 gene of *Y. lipolytica*.

27. A process according to claim 24 wherein said DNA fragment possesses a restriction site unique with respect to the vector such that said vector when cleaved at said site affords double stranded linear DNA having ends homologous to *Y. lipolytica* DNA.

28. A process according to claim 27 wherein said mutation is in the LEU2 gene of *Y. lipolytica*.

29. A process according to claim 28 wherein said *Y. lipolytica* is *Y. lipolytica* having the identifying characteristics of ATCC 20688.

30. A process according to claim 29 wherein said selectable marker is the LEU2 gene of *Y. lipolytica*.

31. A process according to claim 28 wherein said selectable marker is the LEU2 gene of *Y. lipolytica*.

32. A process according to claim 27 wherein said *Y. lipolytica* is *Y. lipolytica* having the identifying characteristics of ATCC 20688.

33. A process according to claim 27 wherein said vector contains the LEU2 gene of *Y. lipolytica*.

34. A process according to claim 28 wherein said *Y. lipolytica* is *Y. lipolytica* having the identifying characteristics of ATCC 20688.

35. A process according to claim 1 wherein said DNA comprises the LEU2 gene of *Y. lipolytica*.

36. A process according to claim 1 wherein said DNA is a vector.

37. A vector which autonomously replicates in *E. coli* and is capable of integrative transformation of *Y. lipolytica*, said vector comprising DNA comprising a region of homology to chromosomal DNA of *Y. lipolytica* sufficient to result in integrative transformation thereof, said DNA being detectable in said *Y. lipolytica*.

38. A vector according to claim 37, said vector comprising a *Y. lipolytica* DNA fragment, which fragment is detectable in *Y. lipolytica*.

39. A vector according to claim 38, wherein said fragment encodes a marker detectable in *Y. lipolytica*.

40. A vector according to claim 38 wherein said *Y. lipolytica* DNA fragment comprises a selectable marker selected from the group consisting of the HIS1, LEU2 and URA3 genes of *Y. lipolytica*, which marker functions in both *E. coli* and *Y. lipolytica*.

41. A vector according to claim 40 wherein said *Y. lipolytica* DNA fragment contains a restriction site unique to said vector.

42. A vector according to claim 41 wherein said *Y. lipolytica* DNA fragment is derived from a partial restriction enzyme digest of *Y. lipolytica* chromosomal DNA.

43. A vector according to claim 42 wherein said restriction enzyme is Sau3A.

44. A vector according to claim 43 wherein said *Y. lipolytica* DNA fragment includes said unique restriction site and the selectable marker is the LEU2 gene of *Y. lipolytica*.

45. A transformant comprising a vector according to claim 44 in *Y. lipolytica*.

46. A transformant comprising a vector according to claim 44 in *E. coli*.

47. A transformant comprising a vector according to claim 37 in *E. coli*.

48. A vector according to claim 37 wherein said DNA being detectable in said *Y. lipolytica* encodes a marker detectable in *Y. lipolytica*.

49. An autonomously replicating *E. coli* vector capable of integrative transformation of *Y. lipolytica*, said vector comprising DNA of an *E. coli* plasmid and chromosomal DNA of *Y. lipolytica*, said chromosomal DNA comprising a *Y. lipolytica* DNA fragment functional in both *E. coli* and *Y. lipolytica*, said fragment comprising a selectable marker selected from the group consisting of the HIS1, LEU2 and URA3 genes of *Y. lipolytica*.

50. A vector according to claim 49 wherein said *Y. lipolytica* DNA fragment has a unique restriction site.

51. A vector according to claim 50 wherein in said *Y. lipolytica* DNA fragment the selectable marker is the LEU2 gene of *Y. lipolytica*.

52. A vector according to claim 51 wherein said *E. coli* plasmid comprises *E. coli* replicating plasmid pBR322.

53. A vector according to claim 52 wherein said restriction site is a KpnI site.

54. A transformant comprising a vector according to claim 53 in *Y. lipolytica*.

55. A vector according to claim 53 wherein said *Y. lipolytica* DNA fragment is derived from a partial Sau3A digest of *Y. lipolytica* chromosomal DNA.

56. A transformant comprising a vector according to claim 55 in *Y. lipolytica*.

57. A transformant comprising a vector according to claim 55 in *E. coli*.

58. A transformant comprising a vector according to claim 49 in *Y. lipolytica*.

59. A vector according to claim 44 wherein in said *Y. lipolytica* DNA fragment the selectable marker is the URA3 gene of *Y. lipolytica*.

60. A vector according to claim 59 wherein said *E. coli* plasmid comprises *E. coli* replicating plasmid pBR322.

61. A vector according to claim 60 wherein said *Y. lipolytica* DNA fragment is derived from a partial Sau3A digest of *Y. lipolytica* chromosomal DNA.

62. A transformant comprising a vector according to claim 59 in *E. coli*.

63. A process for preparing a vector capable of integrative transformation of *Y. lipolytica* which comprises:
    (a) linearizing plasmid pBR322 with a restriction enzyme; and
    (b) ligating said linearized pBR322 with DNA comprising a region of homology to chromosomal DNA of said *Y. lipolytica* sufficient to result in integrative transformation thereof, said DNA being detectable in said *Y. lipolytica*.

64. A process according to claim 63 wherein said DNA comprises chromosomal DNA obtained from *Y. lipolytica* by digestion thereof with a restriction enzyme.

65. A process according to claim 64 for preparing a *Y. lipolytica* transforming vector which comprises
    (a) linearizing plasmid pBR322 with BamHI;
    (b) obtaining chromosomal DNA from *Y. lipolytica* by digestion thereof with BamHI or Sau3A;
    (c) ligating said linearized pBR322 and said digested chromosomal DNA to produce said vector.

66. A process according to claim 65 for preparing a *Y. lipolytica* gene library which comprises
    (a) linearizing plasmid pBR322 with BamHI;
    (b) treating said linearized pBR322 with alkaline phosphatase;
    (c) obtaining chromosomal DNA from *Y. lipolytica* by a partial Sau3A digest thereof;
    (d) ligating said alkaline phosphatase treated linearized pBR322 and said digested chromosomal DNA to produce said vector;
    (e) transforming *E. coli* with the ligation mixture of step (d) to produce transformants comprising a gene library.

67. A process according to claim 66 wherein said *Y. lipolytica* of step (c) is *Y. lipolytica* NRRL Y-1094.

68. A process according to claim 67 wherein DNA in the range of 4–10 kb is harvested from said partial digest.

69. A process according to claim 68 wherein an *E. coli* leuB mutant is transformed by the gene library derived from the ligation product of step (d).

70. A process according to claim 69 wherein said vector is separated from said transformed *E. Coli*.

71. A process according to claim 69 wherein said *E. coli* mutant is *E. coli* JC-355.

72. A process according to claim 70 wherein said *E. coli* mutant is *E. coli* JC-355.

73. A process for cloning genes by complementation of mutations in *Y. lipolytica* which comprises introducing DNA into a *Y. lipolytica* mutant, said DNA comprising a region of homology to chromosomal DNA of said mutant sufficient to result in integrative transformation and DNA sufficient to complement the mutation in said mutant.

74. A process according to claim 73 wherein said DNA comprises a gene library made in a shuttle vector for *E. coli* and for *Y. lipolytica*.

75. A process according to claim 74 wherein said vector replicates autonomously in *E. coli*.

76. A process according to claim 75 wherein said vector comprises a selectable marker selected from the group consisting of the HIS1, LEU2 and URA3 genes of *Y. lipolytica*, which marker functions in both . coli and *Y. lipolytica*.

77. A process according to claim 76 wherein said *Y. lipolytica* has a mutation in the gene corresponding to said selectable marker.

78. Plasmid pLD25, characterized by a restriction endonuclease cleavage map as shown in FIG. 3.

79. The transformant comprising pLD25, the vector according to claim 78, in *Y. lipolytica* having the deposit Accession Number ATCC 20688, said transformant having the identifying characteristics of ATCC 20687.

80. The transformant comprising pLD25, the vector according to claim 78, in *E. coli* JC-355, said transformant having the identifying characteristics of ATCC 39464.

81. Plasmid pLD28 characterized by a restriction endonuclease cleavage map as shown in FIG. 6.

82. Plasmid pLD55 characterized by a restriction pattern as shown in FIG. 8.

83. The transformant comprising pLD55, the vector according to claim 82, in *Y. lipolytica* said transformant having the identifying characteristic of ATCC 20718.

Figure 7:
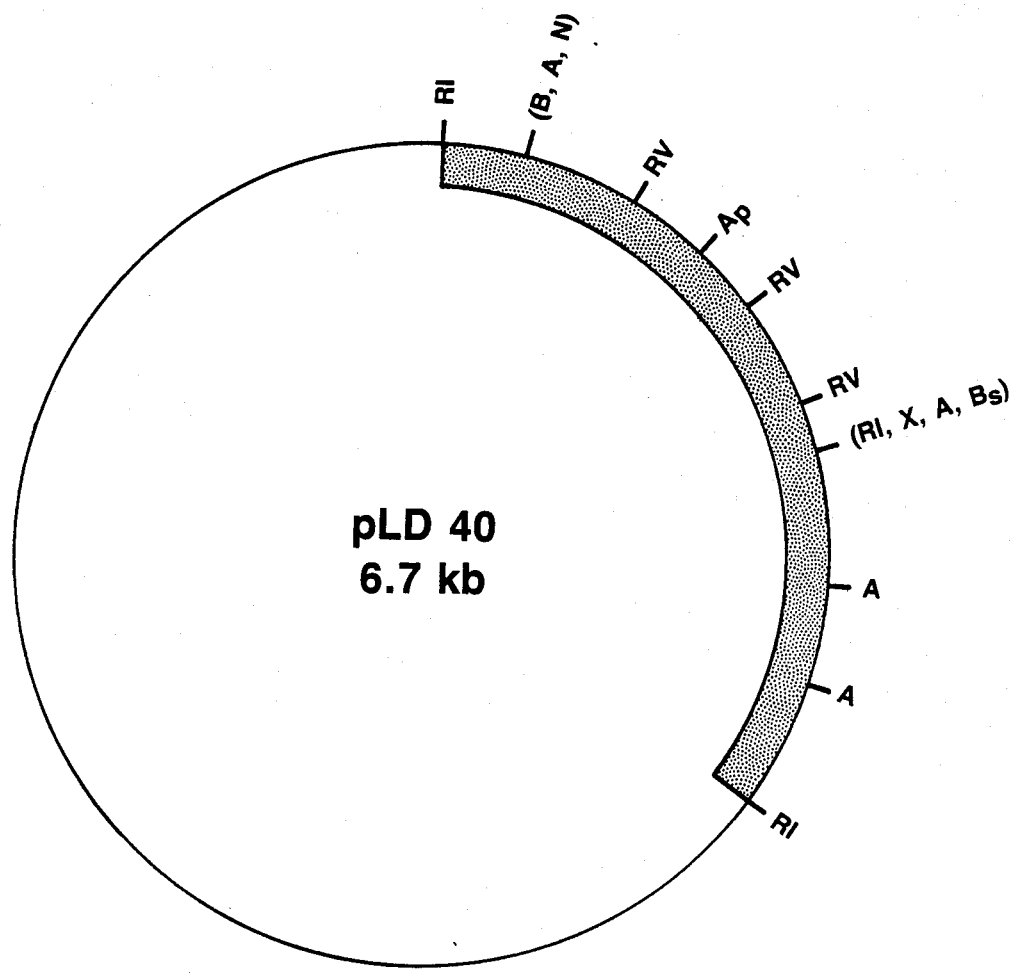

84. Plasmid pLD40 characterized by a restriction endonuclease map as shown in FIG. 7.

85. An autonomously replicating *E. coli* vector capable of integrative transformation of *Y. lipolytica*, said vector comprising DNA of an *E. coli* plasmid and chromosomal DNA of *Y. lipolytica*, said chromosomal DNA comprising a *Y. lipolytica* DNA fragment functional in both *E. coli* and *Y. lipolytica*, said fragment comprising a unique restriction site and the LEU2 and URA3 genes of *Y. lipolytica*.

86. A transformant comprising a vector according to claim 48 in *Y. lipolytica* having a mutation in the gene corresponding to said detectable marker.

87. A transformant comprising a vector according to claim 39 in *Y. lipolytica* having a mutation in the gene corresponding to said detectable marker.

* * * * *

UNITED STATES PATENT AND TRADEMARK OFFICE
CERTIFICATE OF CORRECTION

PATENT NO. : 4,880,741 Page 1 of 1
DATED : November 14, 1989
INVENTOR(S) : Lance S. Davidow et al.

It is certified that error appears in the above-identified patent and that said Letters Patent is hereby corrected as shown below:

<u>Column 23,</u>
Line 67, "14" should read -- 19 --;

<u>Column 25,</u>
Line 41, "44" should read -- 49 --.

Signed and Sealed this

Seventh Day of December, 2004

JON W. DUDAS
*Director of the United States Patent and Trademark Office*